United States Patent [19]
Miller et al.

[11] Patent Number: 5,579,774
[45] Date of Patent: Dec. 3, 1996

[54] METHOD AND APPARATUS FOR MONITORING LOCAL CEREBRAL PHYSIOLOGY

[75] Inventors: John I. Miller, New York; Paolo Bolognese, Brooklyn, both of N.Y.

[73] Assignee: Camino NeuroCare, Inc., San Diego, Calif.

[21] Appl. No.: 206,763

[22] Filed: Mar. 7, 1994

[51] Int. Cl.$^6$ .................................................. A61B 5/02
[52] U.S. Cl. ...................... 128/667; 128/672; 128/748; 128/675; 128/666
[58] Field of Search .............................. 514/78; 364/454; 348/128; 128/633, 748, 736, 742, 691, 634, 665, 666, 667, 673, 675, 661.07–661.1, 662.04; 606/60, 70; 607/126

[56] References Cited

U.S. PATENT DOCUMENTS

| | | |
|---|---|---|
| 3,511,227 | 5/1970 | Johnson . |
| 3,686,958 | 8/1972 | Porter et al. . |
| 4,109,647 | 8/1978 | Stern et al. . |
| 4,210,029 | 7/1980 | Porter . |
| 4,476,875 | 10/1984 | Nilsson et al. . |
| 4,485,820 | 12/1984 | Flower . |
| 4,537,197 | 8/1985 | Hulka . |
| 4,590,948 | 5/1986 | Nilsson . |
| 4,596,254 | 6/1986 | Adrian et al. . |
| 4,608,990 | 9/1986 | Elings . |
| 4,623,789 | 11/1986 | Ikeda et al. . |
| 4,684,245 | 8/1987 | Goldring . |
| 4,730,622 | 3/1988 | Cohen ................................ 128/748 |
| 4,746,211 | 5/1988 | Ruth et al. . |
| 4,862,894 | 9/1989 | Fujii . |
| 5,007,704 | 4/1991 | McCartney . |
| 5,013,313 | 5/1991 | Surer ..................................... 606/60 |
| 5,014,715 | 5/1991 | Chapolini .............................. 128/672 |
| 5,414,509 | 5/1995 | Veligdan .............................. 356/349 |

FOREIGN PATENT DOCUMENTS

| | | | |
|---|---|---|---|
| 2851138 | 7/1979 | Germany .............................. 128/633 |

OTHER PUBLICATIONS

Perimed Laser Doppler Probes.
16th Annual Post–Graduate Course, New York City, 1992, Neurosurgey, Dec. 7–10, 1992.
PeriFlux System 4000, Real–time evaluation of microvascular perfusion.
Laser–Doppler Flowmetry in Neurosurgey, Paolo Bolognese, John I. Miller, Ian M. Heger and Thomas H. Milhorat, Dept. of Neurosurgery, State University of New York Health Science Center at Brooklyn, Brooklyn, NY, Journal of Neurosurgical Anesthesiology, vol. 5,, No. 3. pp. 151–158, 1993 Raven Press, Ltd., New York.

Primary Examiner—Angela D. Sykes
Assistant Examiner—Stephen Huang
Attorney, Agent, or Firm—Morgan & Finnegan, L.L.P.

[57] ABSTRACT

An apparatus for continuous monitoring of cerebral blood flow and intracranial pressure for substantially the same local region of cerebral tissue. A combined probe includes an elongated housing member that contains an ICP probe and a single optical fiber LDF microprobe. The LDF probe and the ICP probe are situated adjacent to each other within the elongated housing member, and preferably their respective intracranial ends are flush with the distal end of the elongated housing member. In addition, the combined probe is adapted to cooperate with an intracranial access system for securing the combined probe, and mitigating movement artifacts. In another embodiment, a combined probe includes a tissue oxymetry probe thus providing both metabolic and hemodynamic information for the same locus of cerebral tissue, and may be used for measuring a local cerebral metabolic rate. Another embodiment of the present invention provides a probe structure that includes a plurality of LDF microprobes for measuring CBF at spatially separate locations. In accordance with the present invention, a system and methods based on multi-modality monitoring, including monitoring of CBF and ICP for the same locus of cerebral tissue, are provided for measuring and assessing physiological processes and parameters including: autoregulation, cerebral vascular resistance (CVR), and carbon dioxide ($CO_2$) reactivity.

31 Claims, 5 Drawing Sheets

METHOD AND APPARATUS FOR MONITORING LOCAL CEREBRAL PHYSIOLOGY

TECHNICAL FIELD

This invention relates generally to a method and apparatus for monitoring physiologic parameters of cerebral tissue, and more particularly to an intracranial fiberoptic probe for bedside insertion which includes laser Doppler flowmetry for continuous monitoring of cerebrovascular microcirculation and further, to a single probe structure for continuous monitoring of both intracranial pressure and microcirculation.

BACKGROUND OF THE INVENTION

Until recent years, assessment of the cerebrovascular status in intensive care unit (ICU) patients has been confined to the determination of cerebral perfusion pressure (CPP) using intracranial pressure (ICP) measurements. New techniques for cerebrovascular assessments include thermal diffusion flowmetry (TDF), which has been used in the ICU owing to the availability of a new generation of probes. The instrument is compact, functions in real time, and provides regional cerebral blood flow (rCBF) data in absolute units (e.g., ml/100 g/min). However, intracranial placement requires intraoperative access which limits monitoring to operative cases. Other obstacles include: suboptimal coupling between the gold plates and cortical surface; repeated local heating of cortical tissue; and only mean values are given without the capacity to visualize a waveform; and as mentioned rCBF is monitored as opposed to the microcirculation (i.e., 1CBF).

Another new technology is transcranial Doppler (TCD) velocimetry in which instruments are equipped with continuous monitoring probes that measure the velocity of blood flow in large intracranial conductance vessels. Weber et al., (Weber M, et al., *Neurosurgery* 1990;27:106–12) were able to distinguish vasospasm from hyperemia in high velocity ranges using Lindegaard et al.'s approach (Lindegaard KF, et al., *Stroke* 1987;18:1025–30). The limitation of TCD velocimetry is that it does not measure microcirculation, but it summates large areas of blood flow and thus, may not "see" the injury or "hot spot." Additional concerns are that the TCD probe is not adequately fixed and may lose its target during ICU monitoring. Nursing procedures and surgical wound sites may introduce further interference.

Yet another technology which may be used for measuring CBF is laser doppler flowmetry (LDF). Under experimental conditions, LDF measurements have compared favorably with other methods for measuring CBF, including radiolabeled microspheres, hydrogen clearance, and quantitative autoradiography. LDF measures the movement of red blood cells (RBCs) within the microcirculation by using the Doppler shift undergone by coherent radiation generated by lasers. Typically, a fiberoptic probe structure is placed in contact with the tissue and guides incident light from the laser source to the tissue, as well as back-scattered light from the tissue to a photodetector within a flowmeter instrument. The flowmeter instrument processes the photodetector signal to elaborate a continuous voltage signal versus time which is linearly proportional to the real blood flow. Some examples of the probe structures, instrumentation, techiques, and signal processing are provided by U.S. Pat. Nos. 4,109, 647, 4,476,875, and 4,596,254. It is well established that the laser emission does not alter microvascular blood flow. A salient attribute of LDF monitoring is that it provides continuous, real-time time signals that have a high spatial and temporal resolution. LDF is compact for bedside use and substantially less expensive than current alternatives which focus on CBF rather than 1CBF. LDF has been used for the evaluation of microcirculatory flow on a variety of tissues including skin, muscle, peripheral nerve, brain, and spinal cord.

Evidently, LDF provides a practical modality for use in an ICU environment for rapid, continuous capillary blood flow assessments with high spatial and temporal resolution. The primary focus of prior investigations and clinical measurements of CBF (e.g., using TCD, TDF, positron emission tomography (PET), single photon emission computed tomography (SPECT), xenon uptake) has been the larger cerebral conductance vessels. In the clinical arena, relatively little attention has been directed towards microvascular cerebral blood flow. The clinical utility of local CBF (1CBF) measurements using flowmetry is currently under investigation as a tool for evaluating cerebral perfusion, and there have been a number of useful LDF studies that focus on microvascular cerebral blood flow. These contributions have delineated important issues regarding the bedside utility of LDF monitoring, as well as the obstacles and limitations which must be overcome.

In 1987 Rosenblum et al. (Rosenblum BR, et at., *J Neurosurg* 1987;66:396–9) performed a single measurement of 1CBF from multiple cortical points surrounding a left parasagittal arteriovenous malformation before and after excision. During these measurements a hand-held probe was used and mean values in absolute flow units ml/100 g/rain) were obtained. Vessels larger than 100 µm produced large aberrant flow values and movement artifacts were frequently encountered. There was fluctuations of flow attributable to vasomotion waves at 6–12 cycles/min.

Further experience with intraoperative LDF was reported by Fasano et al. (Fasano VA, et al., *Acta Neurochir* 1988;95:40–8) on 72 neurosurgical patients. A standard straight surface probe was placed on the surface of the brain and mounted on a self-retaining retractor in the operating room. By attenuating movement artifacts, it was possible to identify three rhythmic variations distinguished by high, medium, and low frequency components. The high component was synchronous with the heart rate; the medium component was synchronous with controlled ventilation; and the low frequency component reflected vasomotion. The effects of various stimuli including pharmacologically induced hypotension, infusion of mannitol, topical administration of nimodipine and papaverine, hypercapnia, and transient cervical carotid artery compression were studied. LDF measurements were also obtained before and after the removal of tumors, cysts, and hematomas.

In 12 patients with superficial brain tumors, Arbit et al. (Arbit E., et al., *Neurosurgery* 1989;24:166–70)used intraoperative LDF to measure 1CBF from normal cerebral cortex and tumor surfaces and compared these results with those obtained during induced hypertension and hypocapnia to evaluate autoregulation and $CO_2$ reactivity. Flow readings were expressed in hHZ (100 Hz) as mean values. Despite transient interruption of controlled ventilation, the quality of the measured signals was impaired by movement artifacts and the presence of light in the operating room. Nevertheless, the authors emphasized that LDF monitoring provides continuous measurements of 1CBF as compared with the episodic data of positron emission tomography and xenon-133 clearance techniques.

In 1991 Mayevsky et al. (Mayevsky A., et al., In: Chance B, Datzir A, eds. *Time-resound Spectroscopy and Imaging of*

*Tissues*, Los Angeles: SPIE 1991:303–13) introduced a multimodality probe that permitted the simultaneous recordings of LDF, NADH redox state, and the concentrations of $K^+$, $Ca^{2+}$, and $Na^+$ in cerebral tissue. These signals were trended in a patient during and after temporary occlusion of a major intracranial vessel through the course of an aneurysm clipping. Clinical recordings were correlated with animal studies to investigate the relationship between metabolic and hemodynamic parameters during ischemic conditions.

Continuous postoperative LDF monitoring was carried out by Hashimoto et al. (Hashimoto T, et al., In: Frowen RA, Brock M, Klinger M. eds. *Advances in Neurosurgery*, vol 17. Berlin: Springer-Verlag, 1989;337–43) on 25 patients with aneurysmal subarachnoid hemorrhage (SAH). LDF probes were placed in the cortex at the time of operation and recordings were obtained intraoperatively and in the ICU that were correlated with epidural intracranial pressure (ICP), systemic arterial pressure (SAP), central venous pressure (CVP), and transcranial Doppler velocimetry (TCD). A special TCD flat probe was used for continuous monitoring of blood flow velocity. Three different signals were recorded from the LDF instrument: flow signal, velocity signal, and volume signal, which equals concentration of moving blood cells (CMBC). Variations of 1CBF were described that were synchronous with the TCD and ICP changes.

Additional experience with LDF monitoring in the ICU was reported by Meyerson et al. (Meyerson BA, et al., *Nerosurgery* 1991;29:750–5) on four comatose patients with head trauma (two cases), SAH (one case), and meningioma (one case). The authors used a special probe that is described below. Following intraoperative placement, the probe was tunneled under the scalp to reduce movement artifacts and permit continuous LDF monitoring for intervals of up to 13 days. 1CBF measurements were compared with both ICP variations and the clinical progress of the patient.

In connection with this prior art, special LDF probes have been developed for monitoring in the ICU; however, intraoperative insertion was required. Hashimoto et al. introduced an angular LDF probe containing a 1-cm-diameter steel disk for stability. The probe was positioned intraoperatively on the cortical surface. In the series of 25 patients described above, there were no complications using this probe. Potential complications of this technique include a cerebrospinal fluid fistula following removal of the probe, and interference with computerized tomographic and magnetic resonance examinations due to the steel disk.

A second composite LDF probe was introduced by Meyerson et al. This probe consists of a plastic connecting screw that joins a master probe and a thin disposable microprobe (500–750 μm in diameter). The microprobe is applied to the cortical surface or fixed within cortical tissue at the end of neurosurgical procedures and is tunneled under the scalp for a distance of 10 cm to reduce movement artifacts. This permits continuous LDF monitoring for prolonged intervals. The plastic connecting screw facilitates optical coupling between the master probe and microprobe by maintaining close contact between the master probe and microprobe. A problem encountered by the present inventors in using this probe, however, is that the plastic connecting screw did not maintain constant optic coupling in agitated patients, resulting in an underestimation of flow signals. Also, although inexpensive, the disposable microprobes are fragile and occasionally break.

The prior art related to LDF probes and methods for measuring CBF, then, evince a number of limitations. For instance, all such probes and methods have been limited to intraoperative placement. Further, excessive compression of tissue by the surface probe is a potential cause of local ischemia. Conversely, incomplete contact between the probe and cortical surface can result in underestimating the flow signal. Movement artifacts are common with hand-held probes, and illumination of the cortical surface and the interposition of irrigation fluid and/or blood between the probe and cortical surface may interfere with LDF measurements. Moreover, correlation of LDF measurements with other continuously monitored cerebral physiological parameters (e.g., ICP) has relied on the use of multiple probes that probe different regions of cerebral parenchyma, thus resulting in increased invasion of cerebral tissue, and in inherently decreased correlation between measured parameters due to spatial separation.

In order to overcome these and other limitations of the prior art, and concomitantly, to provide LDF as a modality for measuring 1CBF, to provide novel modalities for assessing local cerebrovascular status, and further to provide novel methods for assessing patient status and clinical care, it is a general object of the present invention to provide an intracranial LDF probe for bedside insertion which provides for continuous monitoring of 1CBF.

A related object of the present invention to provide an improved apparatus for continuous monitoring of cerebrovascular microcirculation using laser Doppler flowmetry.

A further object of the present invention is to provide an intracranial probe, which may be inserted at the bedside and used for continuous monitoring of both cerebrovascular microcirculation and intracranial pressure in the same locus of cerebral tissue.

Another object of the present invention is to provide an intracranial multimodality probe to avoid the use of multiple probes to monitor multiple modalities.

Still another related object of the present invention is to provide an intracranial multimodality probe to minimize the extent and amount of cerebral tissue manipulation required to monitor multiple modalities.

Still a further object of the present invention is to provide, according to information from continuous monitoring of cerebrovascular microcirculation, improved and novel methods for monitoring and evaluating patient response to treatment maneuvers; and further, for assessing patient status earlier, thus allowing intervention when physiologic aberrations are a reversible point.

Yet another object of the present invention is to provide a system and method for continuous cerebral hemodynamic monitoring; and further, using the primary information obtained from continuous cerebral hemodynamic monitoring for the calculation and derivation of additional cerebrovascular parameters that may be vital to optimizing the patient condition.

Still another related object of the present invention is to provide a method for measuring and assessing physiological processes and parameters including: autoregulation, cerebral vascular resistance (CVR), and carbon dioxide ($CO_2$) reactivity, according to measurement of microcirculation and pressure within the same locus of cerebral tissue.

Yet a further object of the present invention is to provide improved methods for titrating or targeting therapeutic maneuvers to optimize cerebral physiologic parameters; and contrawise, to understand when not to use therapeutic maneuvers that may otherwise be harmful.

Yet a further related object of the present invention is to provide a method and system for continuous monitoring of microcirculation parameters and metabolic parameters within the same locus of cerebral tissue.

SUMMARY OF THE INVENTION

According to the present invention, these and other objects and advantages are achieved by an apparatus for continuous monitoring of local cerebral physiology. In an embodiment of the present invention, a combined probe includes an elongated housing member that contains an ICP probe and a single optical fiber LDF microprobe. The LDF probe and the ICP probe are situated adjacent to each other within the elongated housing member, and preferably their respective distal (i.e., intracranial) ends are flush with the distal end of the elongated housing member. In addition, the combined probe is adapted to cooperate with an intracranial access system for securing the combined probe, and mitigating movement artifacts. The combined probe provides ICP information and CBF information for the same locus of cerebral tissue. In another embodiment, a combined probe includes a tissue oximetry probe thus providing both metabolic and hemodynamic information for the same locus of cerebral tissue, and may be used for measuring a local cerebral metabolic parameter. Another embodiment of the present invention provides a probe structure that includes a plurality of LDF microprobes for measuring CBF at spatially separated locations. In accordance with the present invention, a system and methods based on multi-modality monitoring, including monitoring of CBF and ICP for the same locus of cerebral tissue, are provided for measuring and assessing physiological processes and parameters in the cerebral microcirculation including: autoregulation, cerebral vascular resistance (CVR), and carbon dioxide ($CO_2$) reactivity.

BRIEF DESCRIPTION OF THE DRAWINGS

The invention will be described in greater detail below by way of reference to the accompanying drawings, wherein.

DETAILED DESCRIPTION OF THE PREFERRED EMBODIMENT

Before consideration in detail of the present invention, a brief consideration of the principles of LDF and a conventional LDF system is in order.

In a conventional LDF system, monochromatic light from a laser is transmitted through an optical fiber and directed toward a tissue region. Typically, the monochromatic light source operates at a power of less than 1 mW and at a wavelength of 632.8 nm (i.e., He-Ne laser source), although other laser sources (e.g., semiconductor lasers) operating at different wavelengths of interest may be employed. The incident light is backscattered partly from the surrounding tissue and partly from moving blood cells in the microvascular bed, and a portion of this backscattered light is guided by at least one optical fiber to the instrument for photodetection and signal processing. Light scattering by stationary tissue does not impart a Doppler shift in light frequency; however, moving RBC's will impart a Doppler shift in the light frequency. The optical signal received by the photodetector has a broadened spectrum resulting from the Doppler shifting. The initial portion, or moment, of the spectrum is signal processed to yield excellent linear correlation with standardized systems of flow assessment and minimizes inclusion of RBC multiscattering. Excessive RBC multiscattering in larger vessels limits such an LDF methodology to the microvascular beds with vessel diameters of less than 0.1 mm which includes arterioles, capillaries, and venules. Different signal processing methods, which may further depend on modified probe structures, may be employed to extract the flux signal. For example, in U.S. Pat. No. 4,476,875, in order to mitigate the effects of noise, a system includes two photodetectors which receive separate optical signals via respective optical fibers that collect light backscattered at least partially by different RBCs in separate but mutually adjacent tissue regions. The photodetector signals are processed and subtracted (e.g., differentially amplified) to yield a signal which exhibits reduced noise characteristics. LDF instruments, (an LDF instrument usually includes the laser source, the photodetecting means, and the signal processing means), for providing the RBC flux and concentration of moving RBCs (CMBC), are commercially available, for example, from PERIMED AB, Sweden, which manufactures a number of models of flowmeters. A typical LDF probe may contain three optical fibers of which one is for directing laser emission to the tissue and the remaining two are for receiving backscattered light from the tissue and guiding it to photodetecting means. Widening the distance between the transmitting and receiving optical fibers tends to increase the measuring depth from which the scattered light is received.

Figures 1, 1A:
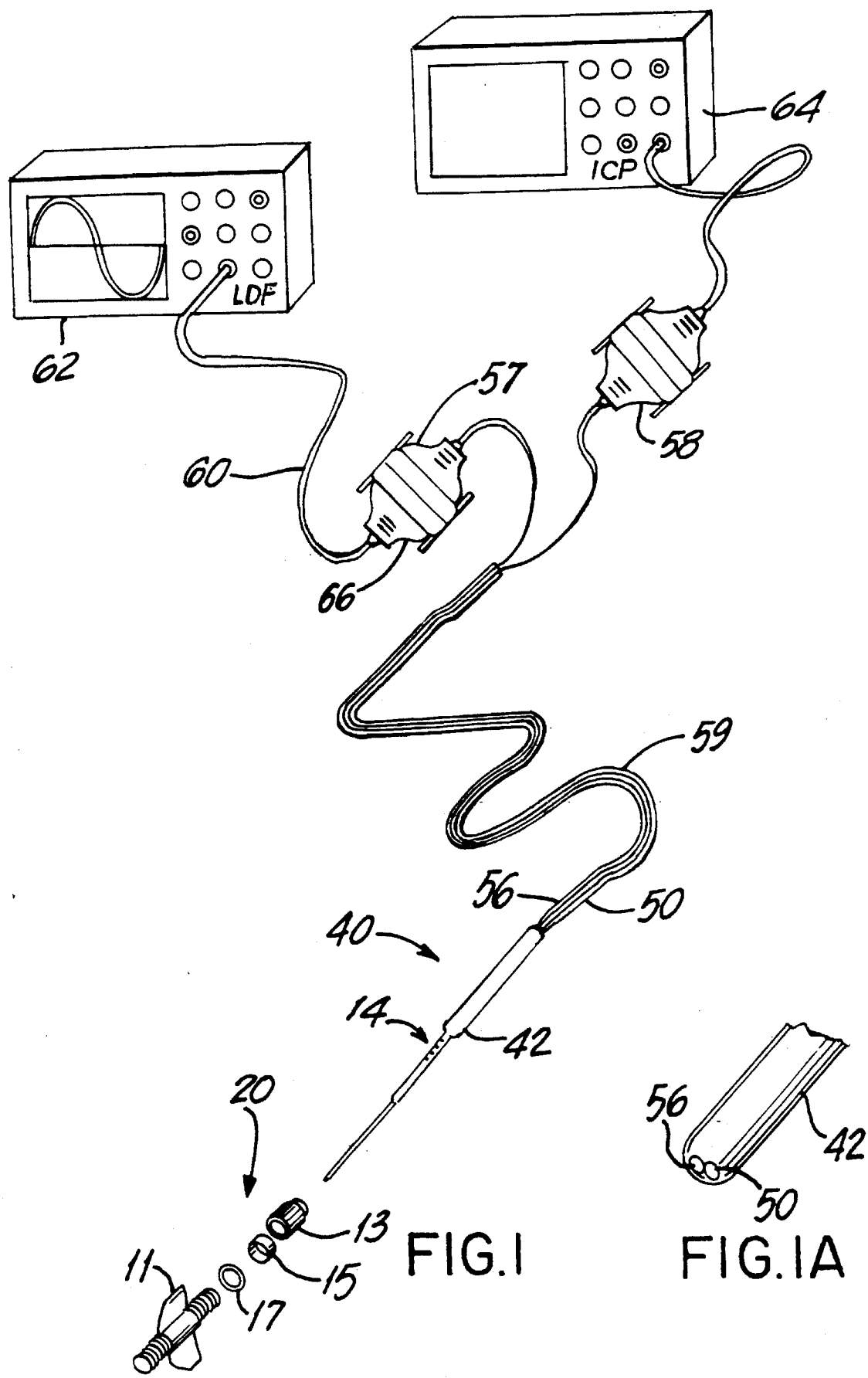
FIG. 1 illustrates a perspective view of a combined LDF/ICP probe in accordance with the present invention, including additional system components for practicing the present invention.
Figure 2:
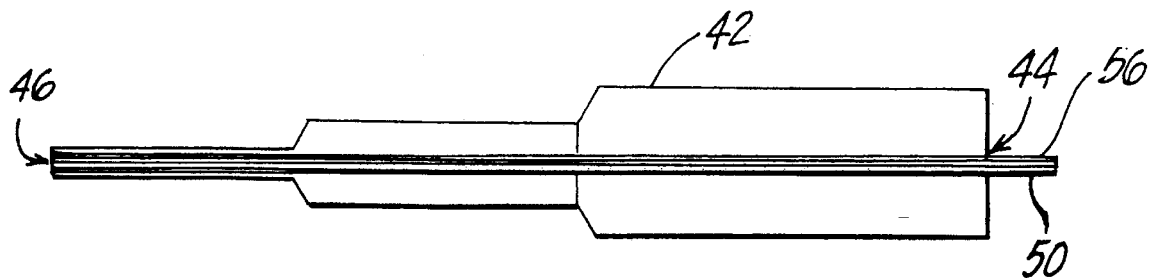
FIG. 2 illustrates a cross-sectional view of the combined LDF/ICP probe according to an embodiment of the present invention.

In accordance with an embodiment of the present invention, FIG. 1 and FIG. 2 show a perspective and cross-sectional view, respectively, of a combined LDF/ICP probe 40 which provides the capability of measuring ICP and microvascular flow within the same locus of cerebral tissue. FIG. 1 further includes other components of a system designed in accordance with practicing the present invention, including intracranial access system 20, master probe 60 which includes master prober adaptor 66, adaptors or modules 57 and 58, LDF instrument 62, and ICP instrument 64. The combined probe 40 includes a rigid elongated housing member 42, an ICP probe 50, and an LDF probe 56. The elongated housing member 42 has a passage or lumen extending between a proximal opening 44 and a distal opening 46 at opposite ends of the combined probe 40. It is understood that the elongated housing member 42 may be manufactured from myriad materials including various plastics, metals, and composites. The elongated housing member 42 is designed to be received by the intracranial access system 20, which is further described hereinbelow. Preferably, the combined probe 40 has two increases in diameter along its length, thereby dividing the combined probe 40 into three sections of differing diameter. As will be further understood below, the distal section diameter is sized at the minimum required to house the LDF probe 56 and the ICP probe 50. The central section diameter is sized to be received within a lumen of the intracranial access system 20 and cooperate therewith to provide a secure fit and airtight seal for the intracranial compartment. The diameter of the proximal section is sized greater than the diameter of the central section in order to limit the depth of penetration, for reasons of safety, of the distal end to preferably no more than a predetermined distance (e.g., about one or two centimeters) past the intracranial end of the intracranial access system 20 into the cortical gray matter. In addition, the combined probe 40 preferably includes graduated markings 14 which are used to assist accurate depth of probe insertion.

The LDF probe 56 is a conventional straight LDF probe, such as one available from PERIMED AB, Sweden. It includes a single optical fiber for directing incident light to the tissue and for guiding backscattered light from the tissue. Typically, this optical fibers uses a step-index silica fiber with a core diameter of about 120 μm, a hard cladding layer of 10 μm, and a numerical aperture of 0.37. Such a fiber features flexibility, small bending radius, and provides for a small outer diameter of the overall LDF probe 56, which may be about 0.5 mm or less. The use of a single fiber (hereinafter, "microprobe") LDF probe 56 for guiding both incident and backscattered radiation allows for a minimally sized intracranial segment of the combined LDF probe 40. Of course, LDF probe 56 may include a multiple fiber arrangement as previously described with reference to conventional LDF monitoring, however, it is desirable for the combined probe 40 to have a minimally sized intracranial segment in order to minimize disturbance of the cerebral tissue.

The ICP probe 50 is preferably a transducer-tipped probe such as those manufactured by Camino Laboratories, and typically includes two optical fibers that are used for respectively transmitting incident light to, and receiving reflected light from, a pressure responsive diaphragm at the distal end of the ICP probe 50. The outer diameter of such a probe is typically about one millimeter. Of course, it would also be advantageous to use a microprobe type ICP probe in order to have a minimally sized diameter for the intracranial segment of the combined probe 40.

Both the LDF probe 56 and the ICP probe 50 are situated adjacent to each other within the lumen of the elongated housing member 42, and preferably their respective distal (i.e., intracranial) ends are flush with the distal end of the elongated housing member 42. Within the lumen of the distal end of the elongated housing member 42 there is preferably an acrylic filling to fortify the optical fiber tips of both the ICP probe 50 and LDF probe 56, and to prevent cerebral parenchyma from becoming trapped within the lumen of the intracranial tip of the combined probe 40. This acrylic filling also fixes the ICP probe 50 and LDF probe 56 to the elongated housing member 42, although a bonding means may be used along the length of the lumen for this purpose.

At the proximal end of the combined LDF/ICP probe 40 the LDF probe 56 and the ICP probe 50 emanate from the elongated housing member 42 and terminate into respective adaptors or modules 57 and 58 for connection to instrumentation for processing the respective signals. Preferably, the LDF and ICP fiberoptic cables have reinforced and plastic housing 59 as they travel to their respective adaptors outside the head. It is understood, however, that a single adaptor may be provided for receiving both the LDF probe 56 and the ICP probe 50. This combined adaptor may then either connect to a single instrument, or may function as a T-connector for connecting the respective LDF probe and ICP probe signals to separate instruments. Camino Laboratories provides an ICP instrument for processing the optical signal provided by the ICP probe, while PERIMED AB manufactures an instrument for processing LDF signals. As mentioned above, a single instrument may be manufactured for processing the respective signals, thus suggesting the use of a combined adaptor or module unit.

The master probe 60 includes an optical fiber for directing incident light from the LDF instrument 62 to the microprobe (i.e., LDF probe 56), and at least one other optical fiber for receiving light from the microprobe and guiding it to photodetecting means within the LDF instrument 62. The master probe adaptor 66 is adapted for coupling the optical fibers of the master probe 60 to the microprobe optical fiber. The end of the LDF probe 56 that terminates in adaptor 57 preferably includes a microlens which focuses the laser beam coupled from the LDF instrument 60 via the adaptor 67 onto the fiberoptic core of the microprobe (i.e., LDF probe 56). The focal length of the lens allows only the low order modes of the optical transmitting fiber to be excited. Thus, an effective numerical aperture of 0.15 is achieved at the probe tip. Exciting only the low order modes of the fiber attenuates fiber-movement artifacts which is generated mostly by high order modes.

Also shown in FIG. 1, is an intracranial access system 20. Preferably, and as represented in FIG. 1, the intracranial access system is similar to the intracranial access system manufactured by Camino Laboratories, San Diego, Calif., which is well suited for bedside insertion, is known to most neurosurgeons, and is designed specifically to stabilize and secure a fiberoptic probe and to maintain intracranial sterility. Camino Laboratories manufactures this intracranial access system as part of their intraventricular ICP monitoring kit and intraparenchymal monitoring kit, in which an intraventricular or intraparenchymal catheter is placed directly through the subarachnoid bolt 11 in to the lateral ventricle or parenchyma for continuous ICP monitoring. Elements of the intracranial access system 20 include a subarachnoid bolt 11, a locking cap 13, a constricting ring 15, and an O-ring 17. The subarachnoid bolt 11 is a disposable skull mounting device having a lumen or passage with openings which provide intracranial access when it screwed into the cranium. When the combined probe 40 passes through the elements of the intracranial access system 20 and the locking cap 13 is securely screwed onto the subarachnoid bolt 11, the constricting ring 15, which includes a bore, and the O-ring 17 cooperate to secure the probe and provide an airtight seal around the probe for intracranial sterility and stability, as well as to prevent the introduction of light artifact within the locus of measurement. Such a coupling member is analagous to what is sometimes referred to as a compression fitting.

Figure 3:
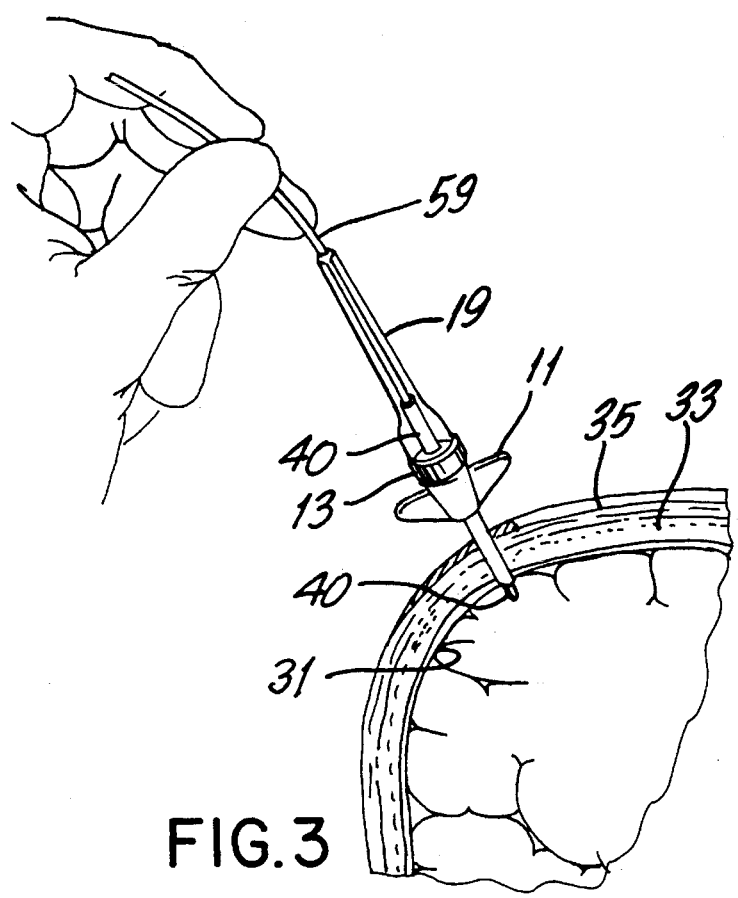
FIG. 3 depicts a combined LDF/ICP probe inserted into the cranium in accordance with the present invention.

Referring to FIG. 3, insertion of the combined probe into the cranium proceeds as follows. At the bedside, under local anesthesia, a twist-drill is performed through the calvarium. Sterile saline is used to flush the twist-drill site and the subarachnoid bolt 11 is screwed into place. The subarachnoid bolt 11 features winged handles which allows the neurosurgeon to torque the bolt into a secure position within the thickness of the cranium 33. Saline is then flushed through the lumen of the fixation cannula and a spinal needle or stylet is passed through the dura. Then, combined probe 40 is inserted to a depth preferably about 1 cm into the cortical gray mantle 11. As described above, the probe includes graduated markings which allows accurate depth placement. The fixation device is locked around the probe to maintain stability and asepsis. Also shown is an optional protective sheath 19, which is a transparent plastic housing that encompasses the section of the LDF probe which extends from the subarachnoid bolt 11, and is used for strain relief as well as for additional sterility. With the combined probe 40 firmly in place, the LDF probe 56 and the ICP probe 50 can be easily connected to, or disconnected from, the instruments 62 and 64 for patient transport to and from the ICU, without affecting the combined probe 40 position. Preferably, after using a combined probe 40, it is disposed of according to standard procedures. The application of a subarachnoid screw with insertion of an intracranial monitoring probe, as described hereinabove, is a standard bedside procedure that is thoroughly familiar to neurosurgeons. It can be appreciated that the foregoing embodiment of the present invention provides for insertion without the need for an intraoperative procedure; for continuous LDF monitoring over extended intervals; for continuous and simultaneous monitoring of both lCBF and ICP; and for minimization of movement artifacts even in the agitated patient.

It is appreciated that in accordance with the present invention, cerebral hemodynamic parameters are made available for patient care. It is thus possible to insert and carry out LDF monitoring on neurosurgical patients in the Intensive Care Unit (ICU), and further it is possible to measure both ICP and CBF from the same locus of cerebral tissue in a continuous manner. The procedure can be combined in a complementary fashion with the use of transcranial doppler (TCD) velocimetry to obtain both regional assessments of CBF (rCBF) with TCE and local CBF (lCBF) measurements of cerebral blood flow with LDF, respectively. LDF continously monitors the hot spot and TCD assesses other regions of the brain. The clinical value of local cerebral hemodynamic trending is increased when the data are correlated with other routinely monitored physiological parameters.

Figure 4A:
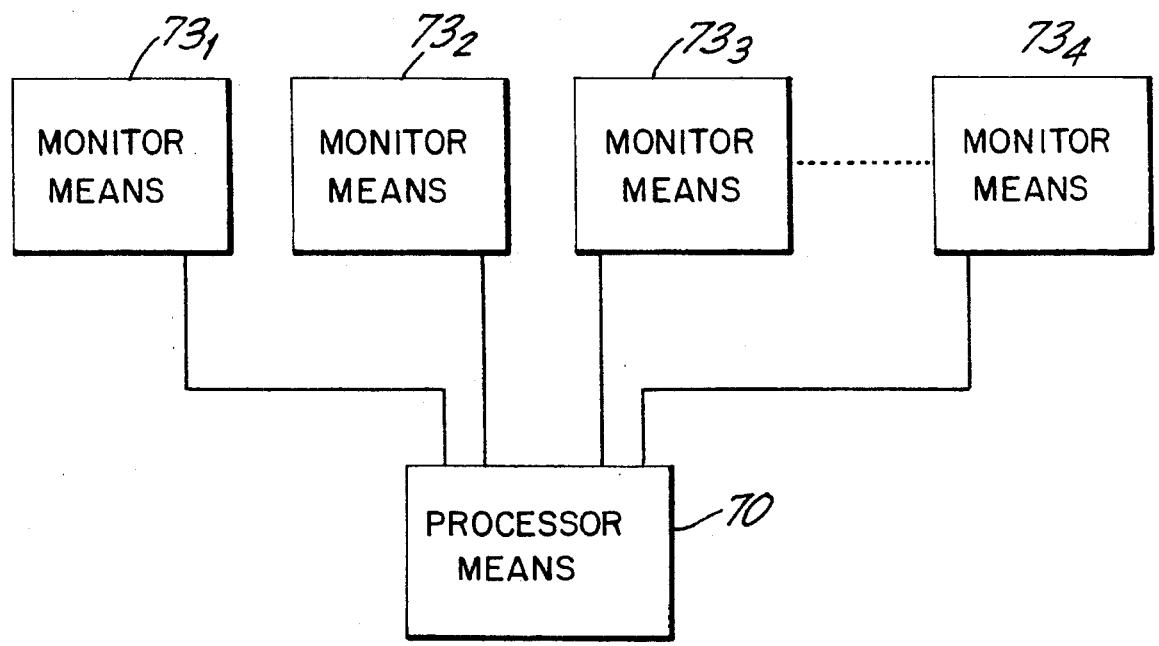
FIG. 4A shows a functional block diagram of a data acquisition and processing system for patient care, which includes processing of local and continuous cerebrovascular information, in accordance with the present invention.

FIG. 4A shows schematically, and by way of example, a functional block diagram of a data acquisition and processing system for consolidating into one computing environment for comparing, displaying, trending, and generally processing, many different physiological parameters, including local CBF monitoring, over extended intervals, thereby providing a methodology for patient care. A processor 70 (e.g., PC) collects data from a variety of monitors $73_1$, $73_2$, $73_3$, ... $73_n$ and processes the data, using the heretofore unavailable continuous lCBF data, or the heretofore unavailable continuous and simultaneous lCBF and ICP data for the same locus of tissue. For example, flow data from the microvasculature can be recorded in a concurrent manner with transcranial doppler assessment, and systemic physiologic parameters including: Swan-Ganz measurements (PAP, CVP, and $SVO_2$); oxymetry; end-tidal $CO_2$; SAP (systemic arterial pressure—arterial line); and any other objects of intracranial monitoring.

As represented by FIG. 4A, the monitors $73_1$, $73_2$, $73_3$, ... $73_n$ may represent separate instruments which are currently available for monitoring different parameters, and include or are adapted to include an output (e.g., analog output, or digital output) and/or a communications bus (e.g., digital communications bus) such that the processor 70 may acquire information therefrom. As understood by one practiced in data acquisition techniques, various conventional digital-to-analog (D/A) converters, analog-to-digital (A/D) converters, amplifier circuitry (e.g., operational amplifier circuits), and related hardware, software, and communications protocols (e.g., IEEE 488/GPIB interface bus) may be required to practice the embodiment represented by FIG. 4A, and more particularly, to interface the various monitors $73_1$, $73_2$, $73_3$, ... $73_n$ to the processor 70. It is further understood that the processor 70 may subsume some of the processing functions and/or control functions for these monitors (e.g., by communicating over a communications bus). Moreover, monitors $73_1$, $73_2$, $73_3$, ... $73_n$ are not necessarily limited to passive monitoring devices, but also may include means for affecting or regulating the patient's physiological parameters. Such control or processing by processor 70 may be desirable in order to efficiently implement such an integrated multi-modality system by centralizing cooperation among the different monitors and other instruments. For instance, processor 70 may provide control signals to respective monitors corresponding to predetermined monitoring parameters (e.g., TCD assessment frequency, ICP/LDF sampling rate, etc.) and/or to implement a particular monitoring sequence and/or maneuver (e.g., hyperventilate patient, increase sampling rate of ICP/LDF monitor, modify $CO_2$ concentration using a respirator, modify intravenous (IV) flow rate, etc.). As an example of processor 70 subsuming some of the processing performed by conventional monitors, consider that instead of using a commercial LDF monitor that processes raw LDF signals to provide CBF and velocity signals, processor 70 may receive and process raw LDF signals via an LDF monitor (e.g., monitor $73_1$) that is adapted only to transmit an optical signal to an LDF probe, receive an optical signal from the LDF probe, and convert the received optical signal to an electrical signal, and provide this signal as an output for acquisition by processor 70. It is recognized, however, that in accordance with the advantages of distributed processing, having each monitor perform processing of the information that it receives from the patient eases the burden on processor 70, allowing processor 70 to focus on providing clinically useful information derived from processing information received from the respective monitors.

Preferably, processor 70 includes a user interface which provides the user or clinician with many preprogrammed functions and options, including graphical display of any of the parameters or functions of the parameters versus time or each other, multivariate regression analysis, spectral analysis, digital filtering, and selection of time intervals for analysis and display. Where a personal computer is employed for processor 70, specialized software is commercially available to correlate the data rapidly and identify event markers that assign a specific cause (i.e., suctioning, turning of patient) to a change in monitored parameters. Such specialized software may be incorporated into an overall software system or environment for real-time and/or offline processing. It is understood, however, that processor 70 represents any processor or processing system, including a specifically designed instrument, that performs the functions described herein; evidently, a specifically designed instrument may include a rack-mounted instrument with plug–in slots for plug–in modules or monitors $73_1$, $73_2$, $73_3$, ... $73_n$ where practical. In accordance with practicing the present invention, the processes and methods used to manipulate the data may include known algorithms which could not be heretofore practiced because of the unavailability of this data, as well as novel algorithms which may be developed in view of the availability of this information, and this processing may in turn yield statistically significant measures or relationships to establish clinical indexes (i.e., a statistically significant parameter or relationship between or among parameters that has prognostic value).

Figure 4B:
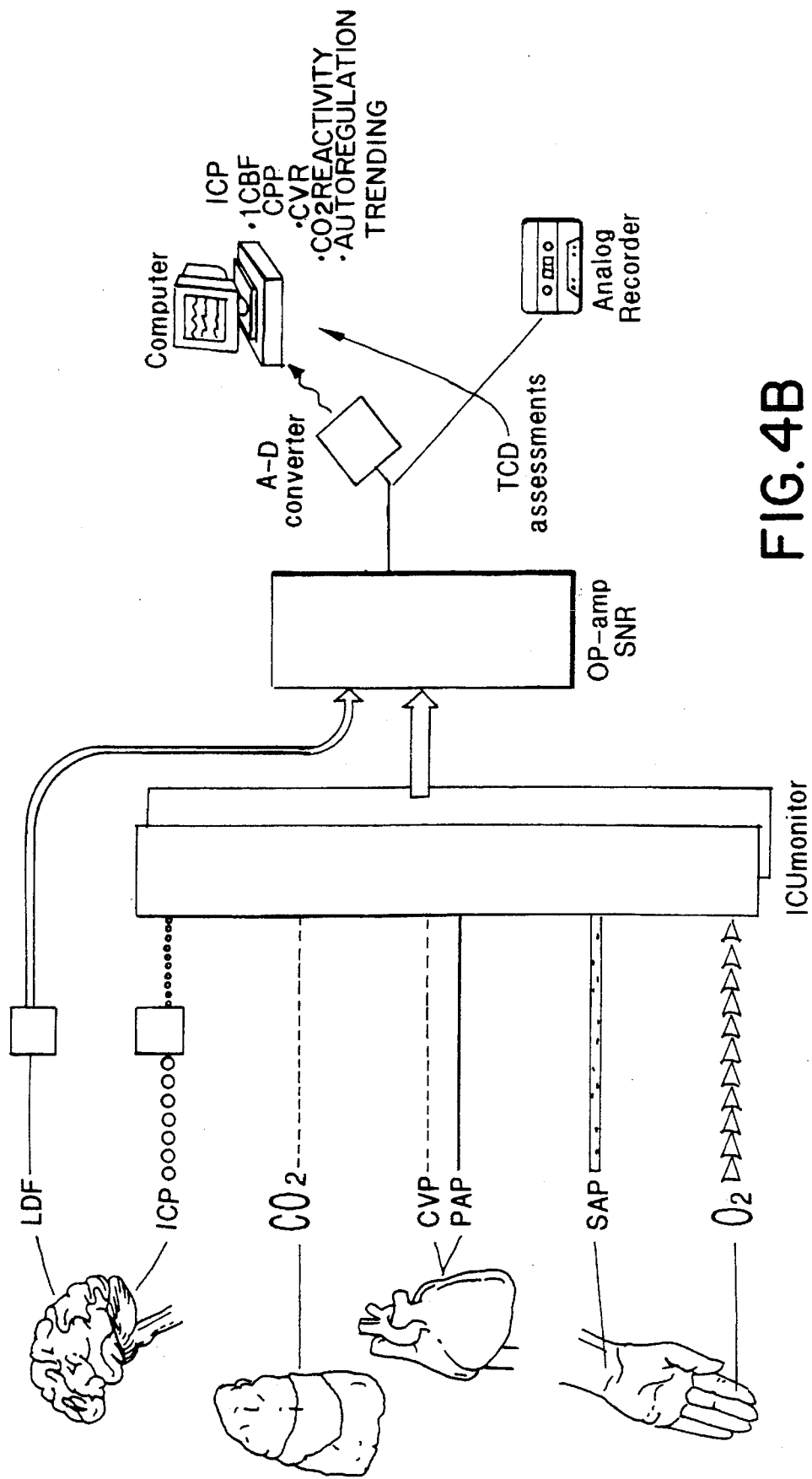
FIG. 4B shows a more detailed embodiment of a data acquisition and processing system for patient care, in accordance with FIG. 4B and the present invention.

A simple example of a parameter which may calculated in accordance with the present invention is the cerebrovascular resistance (CVR) for the locus of tissue sampled by the combined probe 40. In order to calculate a CVR value, in addition to the CBF and ICP information corresponding to signals from the combined probe 40, the processor 70 also receives continuous SAP information via a conventional monitor. Using this information, the CVR may be calculated by the processor 70 by first calculating the difference between SAP and ICP for a given sample time (i.e., CPP= SAP–ICP), and then dividing the CPP value by the CBF value for substantially the same sample time. This CVR parameter may be displayed continuously as a waveform by the processor, and correlated with other physiological parameters. It is evident that temporal averaging, and other digital filtering techniques may be used in accordance with calculating the CVR value, and further, that the changes in CPP and CBF that result in changes in CVR may be correlated with other physiological parameters and patient conditions. That is, for example, an increase in CVR may reflect an increase in CPP, or a decrease in CBF, or both, each possibility attributable to changes in physiological processes that have an effect on the respective parameters, thus implicating different treatment maneuvers where required. Conventional monitoring assumes adequate CBF in the face of normal CPP, however, elevation of CVR may compromise CBF to ischemic levels, despite a normal CPP (i.e., CPP=CBF×CVR). The relationship between the CPP and the CBF, as represented by the CVR, will be further appreciated hereinbelow in connection with autoregulation. The CVR, which could not be measured prior to the present invention, may be analogized to the systemic vascular resistance provided by use of a Swan-Ganz catheter in the heart. Of course, since the CVR depends on both parameters measured by the combined probe, a combined LDF/ICP instrument that subsumes all the functionality of each separate commercial instrument and also includes an input for receiving a SAP signal could readily be adapted to calculate and provide a CVR signal directly to the processor 70, in addition to CBF and ICP signals. This latter combined LDF/ICP instrument is described as an example of a variation that may be provided in the data acquisition and processing system depicted in FIG. 4A, which is merely shown as a general system for acquiring and processing objects of intracranial monitoring, and more generally, combining such intracranial monitoring with continuously monitored systemic physiological parameters. A more particular depiction of an embodiment of a system in accordance with FIG. 4A is the system shown in FIG. 4B, which illustrates some of the hardware that may be required or may be adapted to implement a multi-modality acquisition and processing system that includes continuous intracranial monitoring of hemodynamic parameters in accordance with the present invention.

Since the combined LDF/ICP probe provides both CBF and ICP measurements on a continuous basis for the same locus of cerebral tissue, in accordance with practicing the present invention, a method for assessing autoregulation is also provided. As known by one skilled in the art, autoregulation refers to the process in vascular beds which maintains constant blood flow independent of the perfusion pressure. As described in conjunction with measuring CVR, CPP values are calculated over a given time interval. Linear regression is then calculated over the given time interval for the CBF versus the CPP. This linear regression analysis provides a measure of the correlation between these two values, as well as a measure of the standard error of measurement. These measures, then, provide a direct assessment of autoregulation. For a statistically significant measure, if the correlation is greater than a predetermined value, then autoregulation is lost. It can be appreciated that the method for assessing autoregulation in accordance with the present invention provides a distinct advantage over prior methods for assessing loss of autoregulation which generally require the clinician to perform a maneuver (e.g., pharmocological manipulation of SAP) to alter the patient's condition and observe the result on a measureable parameter which, by its indirect relationship to the autoregulation process, is merely suggestive and not uniquely indicative of autoregulation. As is evident to one skilled in the art of data analysis, or assessing physiological parameters, or both, it may be advantageous to process and represent the regression analysis in a variety of ways. By way of example of the kinds of data analysis and processing that may be performed as part of the linear regression analysis, it can be understood that such a linear regression analysis may be performed for different temporal intervals, and/or performed for CPP values and/or CBF values within certain ranges (e.g., for CPP values outside a certain range, there may not be significant correlation with the CBF although within the range a significant correlation exists), and more generally may be combined with digital filtering of the data. Moreover, the processor 70 may perform this analysis effectively in real-time and provide the linear regression analysis values for display for a given interval or continous series of intervals. These descriptions of data manipulation, analysis, and display for the linear regression analysis are only indicative of the myriad types of processing that may be performed in order to elucidate information having clinical value and devoid of spurious effects.

Also in accordance with practicing the present invention, a method for assessing $CO_2$ reactivity. By trending end-tidal $CO_2$ versus CBF, using regression analysis for example, the local $CO_2$ reactivity within the vascular bed can be assessed. It can be appreciated that the method for assessing $CO_2$ reactivity in accordance with the present invention provides a distinct advantage over prior methods which generally require the clinician to perform a maneuver (e.g., hyperventilation) to alter the patient's condition and observe the result. Further understanding of the methods of assessing autoregulation and $CO_2$ reactivity is provided in an article found in *Journal of Neurosurgical Anesthesiology*, Vol. 5, No. 3, 1993, which is hereby incorporated by reference.

Also in accordance with practicing the present invention, a method for assessing plasticity based on fractal analysis is provided. Fractal analysis of electrocardiogram traces has been applied to evaluating systemic plasticity or chaotic behavior, and thus assessing patient status and providing prediction and early diagnosis of patient condition. Techniques of fractal analysis, including fractal analysis of the frequency spectrum derived via a fast Fourier transform (FFT), may be employed in accordance with techniques discussed in the reference *Fractal Physiology and Chaos in Medicine*, Bruce J. West, 1990, World Scientific Publishing Co., Ppe. Ltd., which is hereby incorporated by reference. Similarly, continuous monitoring of CBF as provided by the present invention, as well as ICP or other continously monitored or calculated parameters (e.g., CVR, spectral components of CBF), provides a basis for applying fractal analysis of this information to assess plasticity or chaotic behavior in the brain tissue which may predict the occurrence of an event before any other observable parameters so indicate.

In accordance with the present invention, technical difficulties involving tissue contact, movement artifacts, and spatial variability are effectively minimized by using an intracortical depth probe which moves as a unit with the brain, thus providing for continuous cerebral blood flow trending of the microvasculature without operating room access. Further, the present invention lends itself to standard bedside neurosurgical practice for intracranial insertion. In addition the present invention also provides a probe for continuous, simultaneous monitoring of both ICP and CBF within the same local region, further providing for novel modalities and clinical indices for assessing patient status and care. In view of the attributes and attendant advantages of the present invention, it can be appreciated that the present invention will not only benefit the many patients who do not require surgery but do have neurologic presentations that mandate intracranial monitoring, but also those patients who do require surgery In accordance with the present invention, it can be appreciated that the combined probe 40 may be adapted to include additional probes provided, however, that the overall lateral dimension of the section that is inserted into the cerebral tissue is sufficiently small to minimize damage of the tissue. A rough guideline for this dimension is the dimension of a ventricular catheter, which may range up to about five millimeters. For instance, a conventional tissue oxymetry probe, which typically have dimensions on the order of the ICP probe, may be included into the combined probe or substituted for the ICP probe. Other probes that may be included or substituted include probes for measuring pH, temperature, mobile ions, etc. It can also be appreciated that where a given probe employs multiple optical fibers, it may be possible to adapt the probe to employ a single fiber, microprobe in order to minimize the overall lateral dimension of the combined probe. The incorporation of a tissue oxymetry probe would not substantially affect the overall combined probe design, and thus, a combined probe including oxymetry is also adequately represented by FIG. 1 and FIG. 2. One skilled in the art currently may practice a procedure which requires inserting a jugular venous catheter in order to calculate an arterial venous difference of oxygen ($AVDO_2$) to the brain, and thus assess the overall cerebral metabolic rate ($CMRO_2$) of the brain which has been shown to be of value in the course of patient treatment. The focus of this configuration would be to measure the oxygen content in the cerebral tissue, not in the hemoglobin. It can be appreciated that a combined probe which includes an oxymetry probe and an LDF probe may not only be used for continuous assessment of local metabolism, but also for monitoring and establishing a relationship between CBF and metabolism on a local level by using, for example, regression analysis to assess the coupling between local $CMRO_2$ ($lCMRO_2$), or an extraction value for $O_2$ in the tissue, and CBF. Further, the clinician may monitor this information directly when performing a treatment maneuver (e.g., to increase $O_2$ concentration within the "hot spot" locus).

Figure 5:
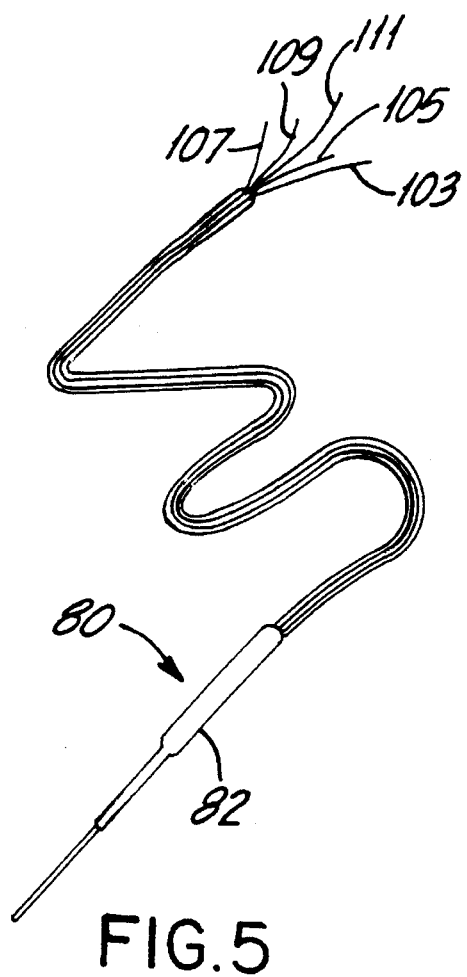
FIG. 5 is another embodiment of a combined probe, specifically adapted for measuring cerebral blood flow in a plurality of local regions, in accordance with the present invention.
Figure 5A:
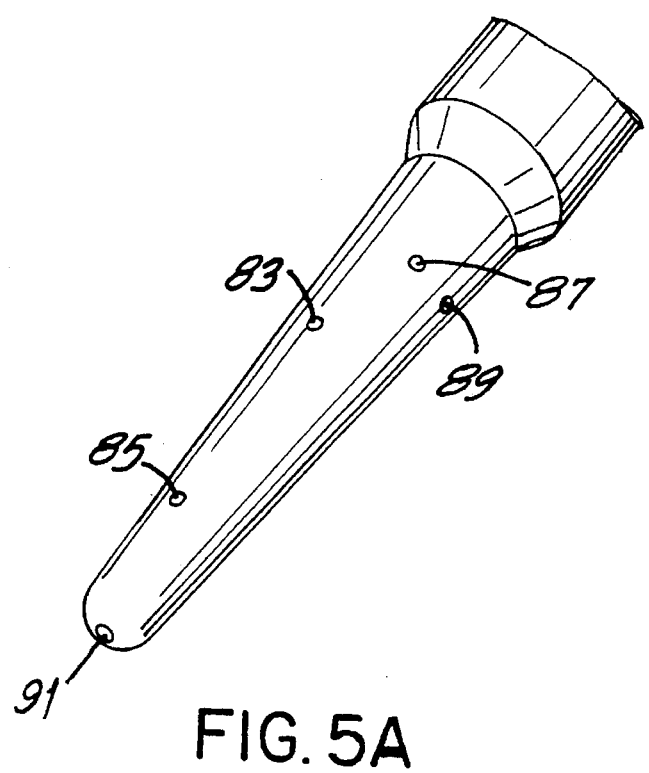

FIG. 5 illustrates another embodiment of a combined probe 80, in accordance with the present invention. As shown, the combined probe 80 includes an elongated housing member 82, which is analagous to the elongated housing member 42 described hereinabove, and further includes a plurality of openings spaced along the length of the elongated housing member 82 at a given azimuth about the axis defined by the length (i.e., openings 83, and 85), and/or spaced azimuthally (i.e., compare openings 87, and 89). Preferably, the outer surface of the distal section of elongated housing member 82 is tapered with decreasing lateral dimension toward the distal end such that successive openings spaced along the length at a given azimuth are spaced in the radial direction by about the diameter of a microprobe fiber. It is understood that for openings at different azimuths such tapering is not necessarily consequential, and the desired tapering, if any, depends on the microprobe arrangement and the desired positions of the openings. Preferably, combined probe 80 may also include an opening 91 at the distal end for exposing an LDF microprobe and/or an ICP probe in a manner analogous to combined probe 40 shown in FIG. 1 and FIG. 2. The elongated housing member 82 includes at least one passage having at least one opening at the proximal end of the elongated housing member 82 and at least one opening 83, 85, 87, 89, and 91 (e.g., there may be a single passage having one opening at the proximal end and having openings 83, 85, 87, 89, and 91; or there may be a separate passage, having an opening at the proximal end and one of the openings 83, 85, 87, 89, and 91 at the opposite end, for each LDF microprobe; etc.). For each of these openings 83, 85, 87, 89, and 91, a respective LDF microprobe 103, 105, 107, 109, and 111, extends through one of the at least one openings at the proximal section of the elongated housing 82 and terminates at one of the respective openings. The number of LDF microprobes that can be employed in such a probe, wherein the probe is used for cerebral monitoring, is limited by the practical limitation of minimizing disturbance to brain tissue; a guideline based on the size of a ventricular catheter is described hereinabove. Preferably, the distal ends of the fibers exposed through openings 83, 85, 87, 89 are beveled and include a reflective surface such that light emanates and is received in a direction (e.g., radial direction) which is substantially perpendicular to the length (e.g., longitudinal axis) of the combined probe 80. The spacing of the microprobes along the length is also sufficient such that substantially no light that is emitted from one microprobe and backscattered by the tissue is received by another microprobe. It can be appreciated that as opposed to having an elongated housing member 82, a combined probe equivalent to that shown in FIG. 5 may be formed by integrally joining a plurality of LDF microprobes in the desired spatial arrangement using conventional optical fiber fabrication and/or molding technology. Combined probe 80, then, may be useful for assessing and comparing CBF at different spatial locations proximate to pathological tissue and/or normal tissue, or to compare CBF in gray matter vs. white matter, which may be used as a reference point. The LDF microprobes 103, 105, 107, 109, and ill extend away from the proximal end of the elongated housing 82 and terminte in respective adaptors for coupling each LDF microprobe to a respective LDF instrument or channel, although an integrated adaptor may house the proximal ends of all the LDF microprobes. In addition, it can be understood that one or more ICP or other probes may also be included in such a probe arrangement in direct analogy and in accordance with the detailed description of the LDF microprobes.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope. For example, it can be appreciated that other probe fixation means may be used, and the probe structure adapted accordingly. For instance, the probe structure may be adapted for attachment by flexible clamps or lobes (e.g., U.S. Pat. No. 4,623,789), or detent balls and recesses. The subarachnoid bolt based intracranial access system is shown as the securing means, however, since it is a conventional system familiar to most neurosurgeons which features easy bedside insertion, secure and accurate placement of the fiberoptic probe, and sterility of the intracranial compartment.

In addition, it is understood that in accordance with the present invention other configurations of the optical fibers may be used in such a combined probe, including different numbers of optical fibers, different types of fiberoptic pressure sensors (oriented to measure in different directions), as well as different types of probe sensors (e.g., intraparenchymal oxymetry probes as discussed hereinabove) in combination with LDF or with ICP and LDF. The preferred configuration may be dependent on the instrumentation used for processing the optical signals. For example, some methods and apparatus for measuring blood flow require a plurality of fibers for receiving the backscattered light, while others require only one such fiber.

Moreover, it will be further appreciated that the combined probe may be housed in different ways: for example, instead of using an elongated housing member 42 having a lumen, the fiberoptic cables which respectively comprise the LDF probe and the ICP probe may be integrally joined or molded in a common material (e.g., polyethylene) according to known manufacturing techniques. Further, in such a construction, the material of the elongated housing member 42 may be the same or different than the material of the cladding of the optical fibers, and the sheath 12 may include more than one layer. For instance, an inner sheath layer of a first material may be integrally joined with the cladding of the optical fibers, and an outer sheath or jacket layer of a second material (e.g., polyethylene) may encase the inner sheath. It can be appreciated that such a multilayer approach may be particularly desirable for a section which cooperates with the intracranial access system in order to provide desirable properties for this probe section in contrast to the remaining length. Such properties may include increased mechanical strength, rigidity, or resistance to sterilization chemicals, in addition to assisting the manufacture of the geometric and any other mechanical features needed to couple with a given intracranial access system. Also, if both the LDF probe and the ICP probe each are sufficiently rigid and mechanically strong then it may not be necessary for a housing to enclose them along the distal section that is inserted into the cranium, thus minimizing the diameter of the probe section inserted into the cerebral parenchyma. That is, the housing which combines the LDF and ICP probes is only required to extend along a section of the combined probe that cooperates with the intracranial access system to provide secure fixation of the combined probe; at the distal end the LDF and ICP fiberoptic probes extend beyond the housing (preferably, however, along this "unhoused" distal section the LDF probe and ICP probe are continuously joined such that cerebral parenchyma does not become trapped between them). In general, then, myriad manufacturing techniques may be used to fabricate the combined probe structure, and these techniques may be used to tailor the properties of different sections of the probe according to the desired or required properties thereof.

These modifications represent obvious adaptations of the present invention, and are provided as several examples of such modifications, but are not intended to be restrictive thereof or limiting of the advantages which can be achieved by the invention. These and other changes can be made without departing from the spirit and the scope of the invention and without diminishing its attendant advantages. It is therefore intended that the present invention is not limited to the disclosed embodiments but should be defined in accordance with the claims which follow.

We claim:

1. A probe, having a proximal and distal end, for intracranial monitoring of pressure and blood flow in a locus of a tissue medium proximately located at the distal end, said probe comprising:
   a first optical conductor, having one end located at said distal end and an opposite end located at said proximal end, that guides radiation to said distal end and guides radiation scattered from said tissue medium to said proximal end for providing a first indicative of the blood flow in the locus of the tissue medium; and
   a second optical conductor, having one end including a pressure responsive means located at said distal end, adapted for generating an second optical signal at an opposite end located at said proximal end, said optical signal indicative of said pressure in the locus of the tissue medium;
   wherein said first signal indicative of the blood flow in the locus of tissue medium and second optical signal indicative of said pressure in the locus of the tissue medium are measured substantially simultaneously and continuously
wherein sections of respective said optical conductors extending from said respective one ends of said first and second optical conductors, are movable together, providing an elongated integral section.

2. The probe according to claim 1, wherein said respective optical conductors form said elongated integral section in a common sheath.

3. The probe according to claim 1, further comprising an elongated housing member having proximal and distal ends and at least one elongated passage with proximal and distal openings, said first and second optical conductors extending within said at least one elongated passage and being fixed to said elongated housing member.

4. The probe according to claim 3, wherein said first and second optical conductors extend through said proximal opening to provide a proximal section of optical conductors outside of said elongated housing member.

5. The probe according to claim 3, wherein said first and second optical conductors extend through said distal opening to provide a distal section of optical conductors outside of said elongated housing member.

6. The probe according to claim 3, further comprising an adhesive compound for fixing said first and second optical conductors to said elongated housing member.

7. The probe according to claim 3, further comprising a fixation member adapted for fixable mounting to a member having a bore, said member having a fixed adjacently disposed spatial relationship with said tissue medium, said fixation member having a lumen with proximal and distal openings, wherein said fixation member is mounted to said member such that said lumen is aligned with said bore, said proximal opening disposed away from said tissue medium and said distal opening disposed toward said tissue medium and wherein said elongated housing member is sized to be received within the lumen of said fixation member.

8. A probe for intracranial monitoring of pressure and blood flow at a local region of a tissue medium adjacently disposed to a distal end of said probe, comprising:
   pressure transducer means including a first optical fiber means and a pressure responsive member which cooperate to produce an first optical second signal indicative of said pressure in said local region of the tissue medium, said pressure responsive member located at one end of said first optical fiber means; and
   second optical fiber means for laser doppler flowmetry to provide a signal indicative of blood flow in said local region of the tissue medium, said second optical fiber means having one end movable together with, and adjacently disposed to, said one end of said first optical fiber means, thereby forming an elongated integral section; wherein said first optical signal indicative of said pressure in said local region of the tissue medium and second signal indicative of blood flow in said local region of the tissue medium are measured substantially simultaneously and continuously.

9. The probe according to claim 8, further wherein a member having a fixed bore has a fixed adjacently disposed spatial relationship with said tissue medium, sad probe comprising a fixation means adapted for fixable mounting to said member, said fixation means having a lumen with proximal and distal openings, wherein said fixation means is mounted to said member such that said lumen is aligned with said bore, said proximal opening disposed away from said tissue medium and said distal opening disposed toward said tissue medium and wherein said elongated integral section is sized to be received within the lumen of said fixation means.

10. A probe apparatus for measuring intracranial pressure and blood flow in a locus of a tissue medium adjacently disposed to a distal end of said probe apparatus, comprising:

a fixation member adapted for fixable mounting to a cranium having a bore, said fixation member having a lumen with proximal and distal openings, wherein said fixation member is adapted to be mounted to said cranium such that said lumen is aligned with said bore, said proximal opening disposed toward an exterior of said cranium and said distal opening disposed toward an interior of said cranium;

an elongated housing member sized to be received within the lumen of said fixation member and having proximal and distal ends and at least one elongated passage with proximal and distal openings;

a pressure transducer member including a first optical fiber member and a pressure responsive member which cooperate to produce an optical signal indicative of said pressure in said locus of the tissue medium, said pressure responsive member located at one end of said first optical fiber member, said pressure transducer member positioned at least partially within said at least one elongated passage with said pressure responsive member located at said distal end of said elongated housing member; and a second optical fiber member for laser doppler flowmetry of said medium to provide an optical signal indicative of blood flow in said locus of the tissue medium, said second optical fiber member positioned at least partially within said elongated passage, and having one end located at said distal end of said elongated housing member, whereby said signal indicative of blood flow and said signal indicative of pressure are both obtained from said locus of the tissue medium wherein said first optical signal indicative of said signal indicative of blood flow in said locus of the tissue medium are measured substantially simultaneously and continuously.

11. The apparatus according to claim 10, wherein said fixation member includes a compression fitting for fixing said elongated housing member when said elongated housing member is positioned within said lumen of said fixation member.

12. The apparatus according to claim 10, wherein said elongated housing member includes a position marker for indicating position of the distal end of said elongated housing member.

13. The apparatus according to claim 10, wherein said first optical fiber member and said second optical fiber member are integrally formed.

14. A probe for intracranial monitoring of pressure and blood flow in substantially the same locus of a tissue medium adjacently disposed to a distal end of said probe, comprising:

optical fiber means for laser doppler flowmetry of said medium to provide an optical signal indicative of blood flow in said locus of the tissue medium; and pressure transducer means coupled to said optical fiber means, said pressure transducer means including an optical fiber and a pressure responsive member for generating an optical signal indicative of said pressure in said locus of the tissue medium.

15. A probe for use in measuring fluid flow at a plurality of local regions of a medium, comprising a plurality of optical fiber means for laser Doppler flowmetry of said medium, said plurality of optical fiber means fixably joined in a predetermined spatial relationship for guiding light to, and receiving backscattered light from, respective said plurality of local regions.

16. The probe according to claim 15, further comprising a pressure transducer means including an optical fiber means and a pressure responsive member for generating an optical signal indicative of pressure exerted against said pressure responsive member, said pressure transducer means joined and movable with said plurality of optical fiber means for laser Doppler flowmetry.

17. A method for continuous monitoring of cerebrovascular blood flow and intracranial pressure of a local region of brain tissue, comprising the steps of:

inserting a fixation means into a cranium, said fixation means having a lumen;

inserting a probe through said lumen of said fixation means, thereby placing a distal end of said probe in proximity to brain tissue, wherein said probe is adapted for being received and secured by said fixation means, and wherein said probe includes a laser Doppler flowmetry probe and an intracranial pressure probe, said intracranial pressure probe having a pressure responsive member located at said distal end;

illuminating said brain tissue by generating an optical signal which is guided by said laser Doppler flowmetry probe to be incident on said brain tissue;

guiding an optical signal along said intracranial pressure probe to said pressure responsive member;

receiving a backscattered optical signal from said tissue and guided by said laser Doppler flowmetry probe;

receiving a reflected optical signal from said pressure responsive member and guided by said intracranial pressure probe;

processing said backscattered optical signal to provide a signal indicative of blood flow within said brain tissue; and processing said reflected optical signal to generate a signal indicative of pressure within said brain tissue.

18. The method according to claim 17, further comprising the step of generating a signal calculated from said signal indicative of pressure and said signal indicative of blood flow.

19. The method according to claim 18, wherein said signal is a cerebrovasular resistance signal for said local tissue region.

20. The method according to claim 17, further comprising the step of generating a signal calculated from fractal analysis of at least one of said signal indicative of pressure and said signal indicative of blood flow.

21. A method for assessing autoregulation for a locus of brain tissue, comprising the steps of:

acquiring a signal indicative of cerebral blood flow from said locus of brain tissue for a time interval;

acquiring an intracranial pressure signal from the locus of brain tissue for the time interval;

processing said signal indicative of cerebral blood flow to generate a cerebral blood flow signal;

processing said intracranial pressure signal to generate a cerebral perfusion pressure signal;

performing regression analysis between said cerebral perfusion pressure signal and said cerebral blood flow signal for said time interval to assess the statistical relationship between said cerebral perfusion pressure signal and said cerebral blood flow signal.

22. A method for assessing carbon dioxide reactivity for a locus of brain tissue, comprising the steps of:

acquiring a signal indicative of cerebral blood flow from said locus of brain tissue for a time interval;

acquiring an end-tidal carbon dioxide signal from a respirator for the time interval;

processing said signal indicative of cerebral blood flow to generate a cerebral blood flow signal;

performing regression analysis between said cerebral blood flow signal and said end-tidal carbon dioxide signal for said time interval to assess statistical relationship between said cerebral blood flow signal and said end-tidal carbon dioxide signal.

23. A probe for use in measuring oxygen content and fluid flow at a local region of a medium adjacently disposed to a distal end of said probe, comprising:

optical fiber means for laser doppler flowmetry of said medium;

tissue oxymetry transducer means, coupled to said optical fiber means, for generating a signal indicative of said oxygen content of said medium.

24. The probe according to claim 23, further comprising optical fiber means for generating an optical signal indicative of pressure of said medium.

25. A system for assessing patient status, comprising:

monitoring means for receiving a plurality of signals, said signals including a signal indicative of cerebral blood flow for a local region of cerebral tissue, and a signal indicative of intracranial pressure for said local region acquired at a time substantially simultaneous to when said signal indicative of cerebral blood flow is acquired;

processing means adapted to acquire from said monitoring means, and for processing, said plurality of signals to assess patient status.

26. The system according to claim 25, wherein said plurality of signals includes a signal indicative of a systemic physiological parameter.

27. The system according to claim 26, wherein said processing means generates a cerebrovascular resistance signal, said physiological parameter being systemic arterial pressure, said cerebrovascular resistance signal equivalent to a ratio between cerebral perfusion pressure and cerebral blood flow, said cerebral perfusion pressure equivalent to a difference between said systemic arterial pressure and said intracranial pressure.

28. The system according to claim 26, wherein said processing means generates a signal indicative of autoregulation for said local region by trending cerebral blood flow and cerebral perfusion pressure.

29. The system according to claim 26, wherein said processing means generates a signal indicative of carbon dioxide reactivity for said local region by trending cerebral blood flow and end-tidal carbon dioxide concentration.

30. The system according to claim 25, wherein said processing means generates a signal based on fractal analysis of at least one said signals indicative of behavior of said local region of cerebral tissue.

31. A system for assessing patient status, comprising:

probe means for guiding to a local region of cerebral tissue, and receiving therefrom, respective optical signals for substantially continuous laser Doppler flowmetry, said probe means capable of being inserted at bedside into a cranium;

means for receiving a plurality of signals, said signals including a substantially continuous signal indicative of cerebral blood flow corresponding to said probe means; and means for processing said plurality of signals to assess patient status.

* * * * *